United States Patent [19]

Voeffray

[11] Patent Number: 4,906,780

[45] Date of Patent: Mar. 6, 1990

[54] PROCESS FOR THE PRODUCTION OF OPTICALLY ACTIVE BETA-METHYLCHOLINE

[75] Inventor: Robert Voeffray, Basel, Switzerland

[73] Assignee: Lonza Ltd., Gampel/Valais, Switzerland

[21] Appl. No.: 149,370

[22] Filed: Jan. 28, 1988

[30] Foreign Application Priority Data

Feb. 4, 1987 [CH] Switzerland ............................ 397/87

[51] Int. Cl.$^4$ ............................................. C07C 91/26
[52] U.S. Cl. .................................................. 564/293
[58] Field of Search ................ 564/293, 302, 303, 304

[56] References Cited

U.S. PATENT DOCUMENTS 2,189,808  2/1940  Major et al. ..................... 564/302 X
3,193,581  7/1965  Shinohara et al. .................. 564/304
3,532,751  10/1970  Langher et al. ..................... 564/292

FOREIGN PATENT DOCUMENTS 0157315  6/1985  European Pat. Off. .
671451  5/1952  United Kingdom ................ 564/302

OTHER PUBLICATIONS

Medicinal Chemistry, vol. 29, No. 7 (1986) p. 1128.
J. Am. Chem. Soc., vol. 57, (1935) p. 2125.
Carbohydrate Research, 16 (1971), pp. 455–458.

Primary Examiner—Robert V. Hines
Attorney, Agent, or Firm—Fisher, Christen & Sabol

[57] ABSTRACT

Process for the production of optically-active beta-methylcholine from optically active 3-chloro-2-oxy-propyltrimethyl ammonium chloride.

17 Claims, No Drawings

PROCESS FOR THE PRODUCTION OF OPTICALLY ACTIVE BETA-METHYLCHOLINE

BACKGROUND OF THE INVENTION

1. Field Of the Invention

The invention relates of a process for the production of optically active beta-methylcholine.

2. Background of the Invention

Optically active beta-methylcholine as an initial product, e.g., for the acetyl derivate or the carbamate, is used in various pharmaceutical preparations [*J. of Medicinal Chemistry*, Vol. 29, No. 7 (1986), p. 1128, or *J. Am. Chem. Soc.*, Vol. 57, (1935), p. 2125].

But so far an advantageous process for the production of optically active beta-methylcholine has been lacking. It was only known to attain the optically active beta-methylcholine by racemate resolution of dimethylaminoisopropanol with expensive (+)-3-bromo-camphor-10-sulfonic acid and further reaction of the optically active dimethylaminoisopropanol with a methyl halide [*J. Am. Chem. Soc.*, Vol. 57 (1935), p. 2125 ff].

Another, very expensive method was composed of attaining the optically active beta-methylcholine by ten steps starting from L-rhamnose [*Carbohydrate Research*, 16, (1971), pp. 455-458].

None of these processes meet the requirement for a technically feasible simple process.

BROAD DESCRIPTION OF THE INVENTION

The object of the invention is to provide an improved process which does not exhibit the drawbacks of the above-described known processes.

The invention involves a new, advantageous process for the production of optically-active beta-methylcholine. The object of the process is achieved by the process of the invention. The process invention includes treating optically active 3-chloro-2-oxy-propyl-trimethyl ammonium chloride with hydrogen in the presence of a base and a hydrogenation catalyst.

By optically active beta-methylcholine, unless otherwise indicated herein, is meant the corresponding optically active beta-methylcholine chloride. But the chloride ion can be exchanged without any problem, e.g. by use of the usual ion exchangers and by other available anions, such as, iodide, bromide or hydroxide.

The optically active 3-chloro-2-oxy-propyltrimethyl ammonium chlorides, i.e., both the (+) and the (−) enantiomers, are simply accessible by a racemate resolution with tartaric acid, according to European Patent Application No. 0,157,315.

Earth alkali or alkali carbonates, bicarbonates, hydroxides or alcoholates are suitably used as bases according to the invention. The alkali metals include lithium, sodium, potassium and casium. The preferred bases are potassium compounds such as potassium carbonate, potassium bicarbonate, potassium hydroxide, potassium methylate and potassium tert-butylate, since the potassium chloride occurring in the reaction is very poorly soluble in the lower aliphatic alcohols, such as, ethanol or methanol, advantageously used as a solvent. But operation can be in water or in a mixture of water with one or more of such alcohols as the solvent.

To obtain a complete reaction 1 to 1.5 equivalents, preferably 1 equivalent, of base is used relative to 1 equivalent of optically active 3-chloro-2-oxypropyltrimethyl ammonium chloride.

A catalyst, such as palladium, platinum or nickel catalysts, can be used as the hydrogenation catalyst. The palladium catalyst, applied to a support material, preferably in an amount of 1 to 10 percent to carbon, the platinum catalyst as platinum oxide or the nickel catalyst in the form of Raney nickel is suitably used. Palladium, 5 percent on carbon, is an especially preferred catalyst. The catalyst is suitably used in an amount between 0.1 to 1 mol percent.

The operation is advantageously performed in a temperature range o 20° to 80° C., especially at 40° to 60° C. and in a pressure range from normal pressure to 40 bars. A pressure between 5 and 10 bars is especially advantageous. With Raney nickel as the catalyst, operation can be done under normal pressure without a problem.

Optionally, the process can proceed so that the optically active 3-chloro-2-oxy-trimethyl ammonium chloride is first reacted with one of the herein-mentioned bases, preferably at room temperature, in one of the herein-mentioned suitable alcohols as the solvent, and only subsequently in a second stage is subjected to treatment with hydrogen in the presence of a hydrogenation catalyst.

After a reaction time according to the invention of 8 to 20 hours, depending on the pressure, catalyst and temperature, the desired optically active betamethylcholine can be obtained as the chloride salt often in yields of over 80 percent after the usual working up.

An optional purification of the relevant optically active beta-methylcholine can take place by a recrystallization from a lower aliphatic alcohol.

If the process according to the invention is performed with R-(+)-3-chloro-2-oxypropyltrimethyl ammonium chloride, S-(+)-beta-methylcholine chloride results; if the operation is with S-(−)-3-chloro-2-oxypropyl-trimethyl ammonium chloride, R-(−)-betamethylcholine chloride results.

DETAILED DESCRIPTION OF THE INVENTION

EXAMPLE 1

Production of S-(+)-beta-methylcholine chloride from R-(+)-3-chloro-2-oxy-trimethyl ammonium chloride 7 g (0.05 mol) of potassium carbonate and 0.2 g of Pd (10 percent on carbon) were added to a solution of 18.9 g (0.1 mol) of R-(+)-3-chloro-2-oxy-trimethyl ammonium chloride ($[\alpha]_D^{24} + 28.8$ (c=1, $H_2O$, mp 208° C.) in 75 ml of methanol in an autoclave. The autoclave was closed, flushed 3 times with $H_2$, put under a pressure of 8 bars of $H_2$, and the mixture was stirred for 16 hours at 50° C. After cooling and opening of the autoclave, the heterogeneous mixture was concentrated to 53 g, the precipitated potassium chloride (7.8 g, 104 percent) and the catalyst were filtered off and washed twice with 8 ml of ethanol each time. The filtrate and the wash ethanol were evaporated. The raw product (15.95 g, 103.9 percent, uniform according to NMR) was suspended in 65 ml of n-butanol for an hour, the heterogeneous mixture was cooled at 5° C. (1 hour), filtered and washed twice with 5 ml of n-butanol each time.

The yield of S-(+)-beta-methylcholine amounted to 11.8 g = 76.9 percent. Other data for the compound is:
Mp: 163°–165° C.
NMR ($d_6$-DMSO, 300 MHz) in ppm
1.11 (d, 3H, $CH_3$);

3.18 (s, 9H, NMe₃);
3.15–3.40 (M, 2H);
4.23 (dddd, 1H, H-C(2));
5.82 (s, H, OH).
$[\alpha]_D^{25} + 38.4$ (c=1, H₂O )

EXAMPLE 2

Production of R-(−)-beta-methylcholine chloride from S-(−)-3-chloro-2-oxy-trimethyl ammonium chloride 10.5 g (0.075 mol) of potassium carbonate and 0.2 g of Pd (10 percent on carbon) were added to a solution of 18.9 g (0.1 mol) of S-(−)-3-chloro-2-oxy-trimethyl ammonium chloride ($[\alpha]_D^{24} - 29.3$ (c=1, H₂O), mp 212° C.) in 75 ml of methanol in an autoclave. The autoclave was closed, flushed 3 times with H₂, put under a pressure of 8 bars of H₂, and the mixture was stirred for 16 hour at 50° C. After cooling and opening of the autoclave the heterogeneous mixture was neutralized within 1 to 5 minutes with 20 ml of HCl/MeOH, was concentrated to 53 g, the precipitated potassium chloride (11.5 g, 102.6 percent) and the catalyst were filtered and washed twice with 8 ml of ethanol each time. The filtrate and the wash ethanol were evaporated. The raw product (15.75 g, 102.6 percent uniform according to NMR) was suspended in 65 ml of n-butanol for an hour, the heterogeneous mixture was cooled at 5° C. (1 hour), filtered and washed twice with 5 ml of n-butanol each time. The yield in R-(−)-beta-methylcholine chloride was 12.1 g–78.9 percent. Other data for the compound is:

Mp: 163°–165° C.
$[\alpha]_D^{25} + 38.4$ (c=1, H₂O)

EXAMPLE 3

Production of S-(+)-beta-methylcholine chloride from R-(+)-3-chloro-2-oxy-trimethyl ammonium chloride 13 g (0.2 mol) of potassium hydroxide (86 percent) and 0.5 g PtO₂ were added to a solution of 37.8 g (0.2 mol) of R-(+)-3-chloro-2-oxy-trimethyl ammonium chloride ($[\alpha]_D^{24} + 28.8$ (c=1, H₂O) mp 208° C.) in 150 ml of methanol in an autoclave. The autoclave was closed, flushed 3 times with H₂, put under pressure of 10 bars of H₂ and the mixture was stirred for 16 hours at 55° C. After cooling and opening of the autoclave the heterogeneous mixture was concentrated to 105.6 g, the precipitated potassium chloride (15.2 g, 102 percent) and the PtO₂ were filtered off and washed twice with 15 ml of ethanol each time. The filtrate and the wash ethanol were evaporated. The raw product (31.8 g, 103.5 percent uniform according to NMR) was suspended in 120 ml of N-butanol for 1 hour, the heterogeneous mixture was cooled at 5° C. (1 hour), filtered and washed twice with 12 ml of n-butanol each time.

The yield of S-(+)-beta-methylcholine chloride was 24.9 g=81.1 percent. Other data for the compound is:
mp: 163°–165° C.,
$[\alpha]_D^{25} + 38.1$ (c=1, H₂O).

EXAMPLE 4

Production of S-(+)-beta-methylcholine chloride from R-(+)-3-chloro-2-oxy-trimethyl ammonium chloride 7 g (0.05 mol) of potassium carbonate and 3.0 g of Raney nickel were added to a solution of 18.9 g (0.1 mol) of R-(+)-3-chloro-2-oxy-trimethyl ammonium chloride ($[\alpha]_D^{24} + 28.8$ (c=1, H₂O) mp 208° C.) in 75 ml of methanol in a hydrogenation apparatus. The vessel was closed, flushed 3 times with H2 and the mixture was stirred for 16 hours at 30° C. under 1 bar of H₂. After cooling the precipitated potassium chloride (7.4 g, 99.3 percent) and the Ni catalyst were filtered off and washed twice with 8 ml of ethanol each time. The filtrate and wash the ethanol were evaporated. The raw product (16.1 g, 104.7 percent uniform according to NMR) was suspended in 65 ml of n-butanol for 1 hour, the heterogeneous mixture was cooled at 5° C. (1 hour), filtered and washed twice with 5 ml of n-butanol each time. The yield of S-(+)-beta-methylcholine chloride was 8.7 g=56.7 percent. Other data for the compound is:

mp: 163°–165° C.
$[\alpha]_D^{25} + 38.0$ (c=1, H₂O)

EXAMPLE 5

Production of S-(+)-beta-methylcholine chloride from R-(+)-3-chloro-2-oxy-trimethyl ammonium chloride A solution of 5.8 g (50 mmol) of potassium tert-butylate in 16.0 g of methanol was instilled into 9.5 g (50 mmol) of (+)-3-chloro-2-oxy-trimethyl ammonium chloride, dissolved in 27.5 g of methanol, at room temperature with stirring. The mixture was stirred for 3 hours, the precipitated potassium chloride (3.95 g, 105 percent) was filtered and washed twice with 5 ml of ethanol each time. The filtrate and wash ethanol were evaporated. The raw product (9.15 g, 119 percent) was taken up in 50 ml of chloroform, and, after shaking, the product gradually dissolved except for some potassium chloride. This insoluble potassium chloride (0.05 g, traces) was filtered. After evaporation of the chloroform the yield of R-(+)-glycidyl trimethyl ammonium chloride was 7.5 g=98 percent. Other data for the compound is:

mp: 119°–121° C.
NMR (d₆-DMSO, 300 MHz) δ in ppm
2.69 (dd, 1H, J=5 and 3 Hz, H-C(3));
2.93 (dd, 1H, J=5 and 5 Hz, H-C(3));
3.22 (dd, 1H, J=13 and 8 Hz, H-C(1));
3.23 (s, 9H, −N(CH₃)3);
3.57 (dddd, 1H, J=8/5/3 and 3 Hz, H-C(2));
4.04 (dd, 1H, J=13 and 3 Hz, H-C(1)).
$[\alpha]_D^{24} + 27.1$ (c=1 H₂O)

0.2 g of Pd (10 percent on carbon) was added to a solution of 6.1 g (40.2 mmol) of R-(+)-glycidyl-trimethyl ammonium chloride ($[\alpha]_D^{24} + 27.1$ (c=1, H₂O) mp 119°–121° C.) in 25 ml of methanol in an autoclave. The autoclave was closed, flushed 3 times with H₂, put under a pressure of 6 bars of H₂, and the mixture was stirred for 16 hours at 55° C. After cooling and opening of the autoclave, the catalyst was filtered off and washed twice with 4 ml of ethanol each time. The filtrate and the wash ethanol was evaporated. The raw product (6.3 g, 102 percent, uniform according to NMR) was suspended in 65 ml of n-butanol for one hour, the heterogeneous mixture was cooled at 5° C., filtered and washed twice with 3 ml of n-butanol each time. The yield of S-(+)-betamethylcholine chloride amounted to 5.3 g=86.1 percent. Other data for the compound is:

Mp: 163°–165° C.
$[\alpha]_D^{25} + 37.2$ (c=1, H₂O).

What is claimed is:

1. Process for the production of optically-active beta-methylcholine comprising treating optically-active 3-chloro-2-oxy-propyltrimethyl ammonium chloride with hydrogen in the presence of a base and a hydrogenation catalyst.

2. Process according to claim 1 wherein the addition of the base and of the hydrogenation catalyst and the treatment with hydrogen take place before the beginning of the reaction.

3. Process according to claim 2, wherein the procedure is by steps, by the reaction first being performed with a base and then treatment with hydrogen taking place in the presence of a hydrogenation catalyst.

4. Process according to claim 3, wherein a base is an alkali earth or alkali carbonate, bicarbonate, hydroxide or alcoholate.

5. Process according to claim 4 wherein a platinum, palladium or nickel catalyst is used as the hydrogenation catalyst.

6. Process according to claim 5 wherein a reaction temperature of 20° to 80° C. is maintained.

7. Process according to claim 6 wherein the operation is conducted in a pressure range of 1 to 40 bars.

8. Process according to claim 7 wherein the operation is conducted in a solvent which is selected from the group consisting of a lower aliphatic alcohol or a mixture of water and at least one lower aliphatic alcohol.

9. Process according to claim 8 wherein R-(−)-beta-methylcholine is produced from S-(−)-3-chloro-2-oxy-propyltrimethyl ammonium chloride.

10. Process according to claim 9 wherein S-(+)-beta-methylcholine is produced from R-(+)-3-chloro-2-oxy-propyltrimethyl ammonium chloride.

11. Process according to claim 1, wherein a base is an alkali earth or alkali carbonate, bicarbonate, hydroxide or alcoholate.

12. Process according to claim 1 wherein a platinum, palladium or nickel catalyst is used as the hydrogenation catalyst.

13. Process according to claim 1 wherein a reaction temperature of 20° to 80° C. is maintained.

14. Process according to claim 1 wherein the operation is conducted in a pressure range of 1 to 40 bars.

15. Process according to claim 1 wherein the operation is conducted in a solvent which is selected from the group consisting of water, a lower aliphatic alcohol or a mixture of water and at least one lower aliphatic alcohol.

16. Process according to claim 1 wherein R-(−)-beta-methylcholine is produced from S-(-)-3-chloro-2-oxy-propyltrimethyl ammonium chloride.

17. Process according to claim 1 wherein S-(+)-beta-methylcholine is produced from R-(+)-3-chloro-2-oxy-propyltrimethyl ammonium chloride.

* * * * *